United States Patent [19]

Melinyshyn et al.

[11] Patent Number: 4,925,452
[45] Date of Patent: May 15, 1990

[54] MULTIPLE CONDUIT DRAINAGE DEVICE

[75] Inventors: Lev Melinyshyn, Mt. Prospect; Edward M. Goldberg, Glencoe, both of Ill.

[73] Assignee: Uresil Corporation, Skokie, Ill.

[21] Appl. No.: 165,623

[22] Filed: Mar. 8, 1988

[51] Int. Cl.⁵ .................................... A61M 27/00
[52] U.S. Cl. ................................ 604/284; 138/111
[58] Field of Search ............ 604/284, 264; 138/103, 138/111, 115, 118; 428/43; 264/159; 29/413; 174/95, 97; 239/450

[56] References Cited

U.S. PATENT DOCUMENTS

| | | |
|---|---|---|
| 2,621,075 | 12/1952 | Sedar ................................ 138/111 |
| 2,624,341 | 1/1953 | Wallace . |
| 3,144,868 | 8/1964 | Jascalevich . |
| 4,072,153 | 2/1978 | Swartz . |
| 4,309,994 | 1/1982 | Grunwald . |

FOREIGN PATENT DOCUMENTS 1082953  6/1960  Fed. Rep. of Germany ........ 174/95

Primary Examiner—Stephen C. Pellegrino
Attorney, Agent, or Firm—Hosier & Sufrin, Ltd.

[57] ABSTRACT

A multiple conduit flexible drainage device in which the adjacent conduits are joined by a plurality of membranes and may be parted from their proximal ends, reliably and without damage to the conduits.

12 Claims, 1 Drawing Sheet

U.S. Patent     May 15, 1990     4,925,452
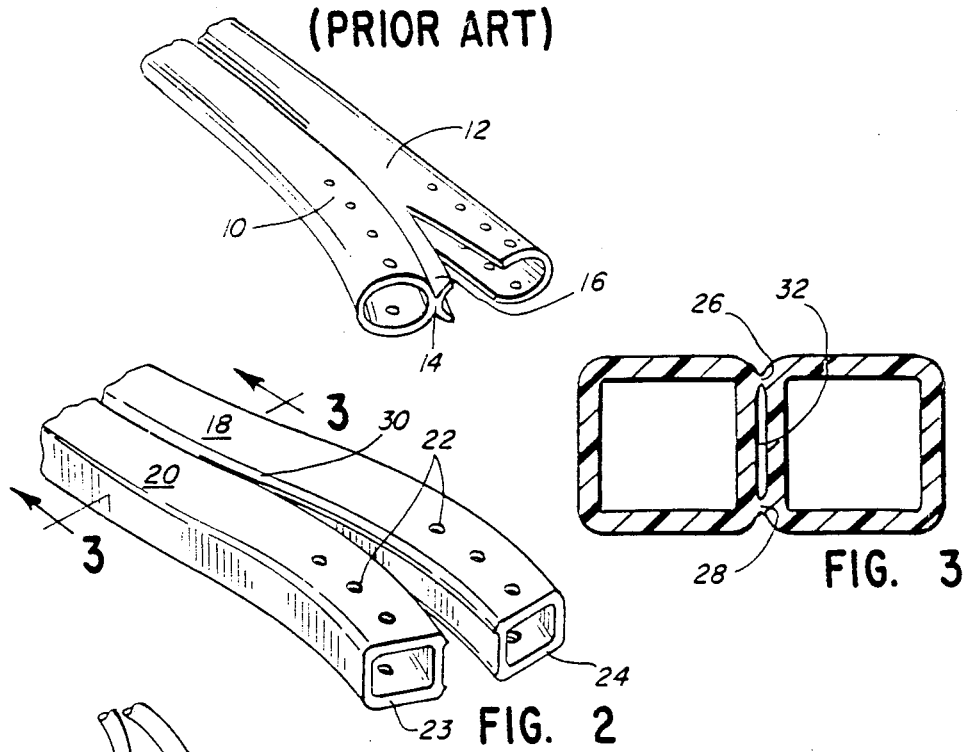
FIG. 1 (PRIOR ART)
FIG. 2
FIG. 3
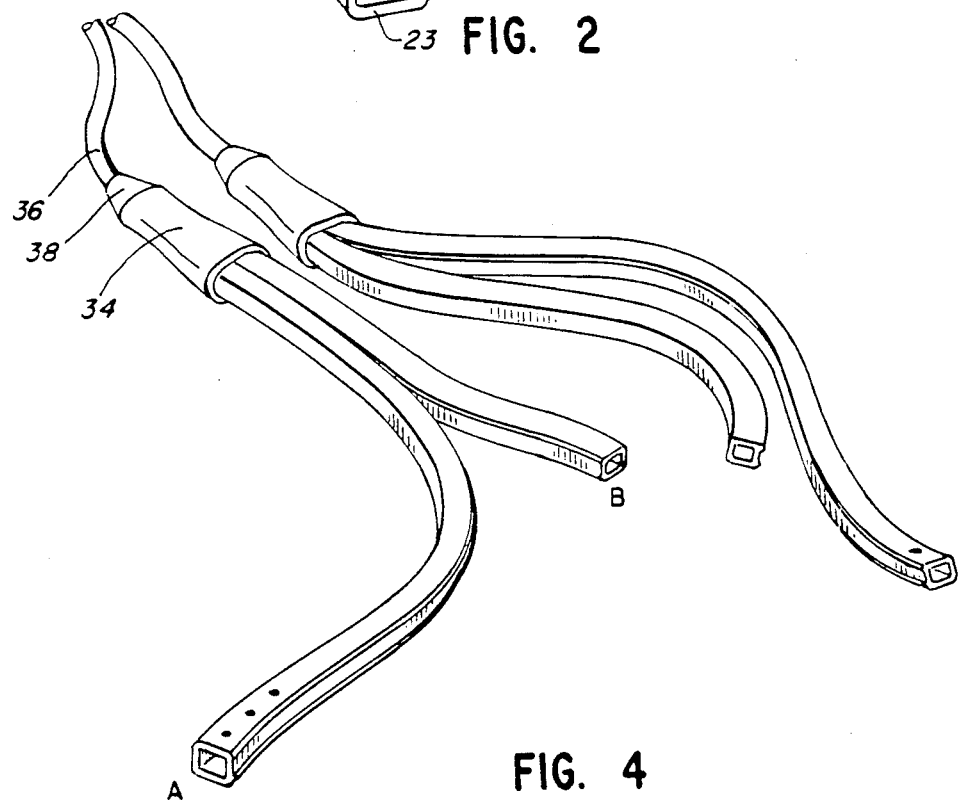
FIG. 4

MULTIPLE CONDUIT DRAINAGE DEVICE

BACKGROUND OF THE INVENTION

This invention relates generally to unitary multiple conduit flexible drainage devices which share a common manifold at their proximal ends. More particularly, this invention relates to unitary multiple conduit flexible drainage devices sharing a common manifold at their proximal ends, in which the individual conduits may be readily parted at their distal ends for routing to different locations.

Multiple conduit drainage devices having a common manifold at their proximal ends are used in many fields, including particularly in the medical field. In a typical medical application, the individual conduits initially are joined along their edges into a unit. The individual conduits are parted, as needed, cut to the appropriate lengths, and routed to the desired locations within a surgical wound site. For example, after surgery is performed on the abdomen, the conduits can be routed separately to the desired abdomen quadrants. Similarly, after a cholecystostomy or a cholecystotomy, separate conduits may be used to drain fluid from the right gutter and Morison's pouch.

In such medical applications, once the conduits are positioned, the wound site is sutured in the manifold under the skin, and a single conduit passing through the wound suture from the manifold to an appropriate gravity or suction drainage device. Thus, as the wound drains, fluid passes from each of the conduits into the manifold and through the single drainage conduit.

Unfortunately, in currently available multiple conduit drainage devices, the individual conduits cannot be readily and reliably parted without damaging adjacent conduits. A multiple conduit drainage device of the type currently available is illustrated in FIG. 1. In this device adjacent conduits 10 and 12 are joined by a single fairly thick membrane 14. When the conduits are separated, a portion 16 of conduit 12 is torn away, rendering the conduit 12 useless, and creating an undesireable ragged appendage on conduit 10.

SUMMARY OF THE INVENTION

It is therefore an object of the present invention to provide a unitary multiple conduit flexible drainage device in which individual conduits may be readily parted.

It is a further object of the present invention to provide a multiple conduit flexible drainage device in which adjacent conduits may be parted reliably, and without damage to any of the conduits.

It is yet another object of the present invention to provide a multiple conduit flexible drainage device in which relative movement of adjacent conduits is minimized.

These and other objects of the present invention will be apparent from the discussion below.

The present invention is therefore directed to a unitary multiple conduit flexible drainage device in which the conduits share a common manifold at their proximal ends for conveying fluid received by the conduits into a common drainage conduit. Each conduit is joined to its adjacent conduits by at least two generally parallel membranes. These membranes may be made thinner and hence more readily frangible than the single joining membrane of the prior art, so that when the distal ends of the conduits are parted, the parting occurs along the membranes, cleanly and without damage to the conduits.

BRIEF DESCRIPTIONS OF THE DRAWINGS

The features of this invention which are believed to be novel are set forth with particularity in the appended claims. The invention, together with its objects and the advantages thereof, may be best understood by reference to the following drawings, in which like reference numerals identify like elements in the several figures and in which:

FIG. 1 is a perspective view of a unitary pair of conduits of the prior art, in which one of the conduits was damaged when an attempt was made to part the conduits;

FIG. 2 is a perspective view of a unitary double conduit flexible drainage device in accordance with the present invention, in which the two adjacent conduits have been parted at their distal end;

FIG. 3 is a cross-sectional view of the conduits of FIG. 2, taken along lines 3—3 of FIG. 2; and FIG. 4 is a perspective view of a unitary multiple conduit flexible drainage device in accordance with the present invention which comprises two conduits, in which the conduits have been parted, cut to the desired lengths, and routed to different locations.

DESCRIPTION OF THE PREFERRED EMBODIMENTS

Although the drainage device of the present invention is described below in connection with a medical application, the invention is believed to be useful in any environment in which it is desirable to have unitary multiple flexible conduits which are commonly manifolded at one end and can be cleanly parted and directed to different locations at their other end.

Turning now to FIG. 2, there are illustrated a unitary pair of conduits 18 and 20 having a plurality of drainage holes 22 to facilitate drainage through the respective distal ends 23 and 24 of the conduits. While only two conduits are shown, the invention will apply to any number of conduits save, of course, a single conduit. Also, although it is preferred that the conduits be rectangular in cross-section, they may be of other geometric shapes such as square, circular or triangular.

As shown in the cross-sectional view of FIG. 3, conduits 18 and 20 are joined by integral membranes 26 and 28, which run the length of the conduits, through the point of parting 30, (FIG. 2). While the present invention requires that at least a pair of generally parallel integrally formed membranes be used, more than two membranes may be used, if desired. The use of multiple membranes joining the adjacent conduits makes it possible to make each of the membranes thinner and more frangible than is possible with a single membrane. This limits movement of the conduits relative to each other for improved handling during manufacture, storage and use. More importantly, when a parting force is applied, the thin membranes break well before the conduits can be damaged.

Another advantage in the use of two or more membranes is the provision of an additional conduit in the space 32 between the conduits, which results in drainage at the parting point 30.

Conduits 18 and 20 are shown, in FIG. 4, in fluid communication with a manifold 34. A common drainage conduit 36 leads from the manifold. As illustrated in FIG. 4, the parted conduits have been cut to the appropriate lengths and routed to the desired locations, A and B.

In the typical medical application, the wound site is sutured at a point in the vicinity of the tapered proximal end 38 of manifold 34, and common conduit 36 is routed to an appropriate drainage device outside of the body (not shown). Thus, only a single wound opening is required to drain fluids from a multiplicity of locations and the size of the opening in the wound necessary for drainage can be kept to a minimum. The conduits and membranes may be made of silicone or of widely available thermoplastics and thermoplastic resins.

While particular embodiments of the invention have been shown and described, it will be obvious to those skilled in the art that various changes and modifications may be made therein without departing from the spirit and scope of the invention, and, therefore, it is intended that the appended claims cover all such changes and modifications which fall within the true spirit and scope of the invention.

What we claim is:

1. A unitary multiple conduit flexible drainage device in which the individual conduits may be parted at their distal ends upon application of a parting force, comprising:
   a common manifold,
   a plurality of generally parallel adjacent conduits, said conduits being in fluid communication with said common manifold at their proximal ends; and
   at least two generally parallel frangible membranes joining adjacent conduits,
   whereby the adjacent conduits may be readily parted from their distal ends.

2. The drainage device of claim 1, in which the conduits are generally rectangular in cross-section.

3. The drainage device of claim 1, in which a pair of generally parallel membranes are used.

4. The drainage device of claim 1, in which the conduits and membranes are made of silicone.

5. The drainage device of claim 1, in which the conduits and membranes are made of thermoplastics or thermoplastic resins.

6. The drainage device of claim 1 in which the membranes are integrally formed with the conduits.

7. The drainage device of claim 1, in which holes are provided in the distal ends of the conduits to facilitate drainage.

8. A unitary multiple conduit flexible drainage device in which the individual conduits may be parted at their distal ends upon application of a parting force, comprising:
   a common manifold,
   a pair of generally parallel adjacent conduits, said conduits being in fluid communication with said common manifold at their proximal ends; and
   at least two generally parallel frangible membranes integrally formed with and joining adjacent conduits,
   whereby the adjacent conduits may be readily parted from their distal ends.

9. The drainage device of claim 8, in which the conduits are generally rectangular in cross-section.

10. The drainage device of claim 8, in which the conduits and membranes are made of silicone.

11. The drainage device of claim 8, in which the conduits and membranes are made of thermoplastics or thermoplastic resins.

12. The drainage device of claim 8, in which holes are provided in the distal ends of the conduits to facilitate drainage.

* * * * *